(12) United States Patent
Caldararo et al.

(10) Patent No.: US 7,745,478 B2
(45) Date of Patent: *Jun. 29, 2010

(54) PERFECTED PROCESS FOR THE PREPARATION OF STABLE NITROXIDE RADICALS

(75) Inventors: Maria Caldararo, Trecate-Novara (IT); Riccardo Po, Leghorn (IT); Marco Ricci, Novara (IT)

(73) Assignee: Polimeri Europa S.p.A., Brindisi (IT)

( * ) Notice: Subject to any disclaimer, the term of this patent is extended or adjusted under 35 U.S.C. 154(b) by 230 days.

This patent is subject to a terminal disclaimer.

(21) Appl. No.: 11/574,582

(22) PCT Filed: Aug. 25, 2005

(86) PCT No.: PCT/EP2005/009236

§ 371 (c)(1),
(2), (4) Date: Mar. 2, 2007

(87) PCT Pub. No.: WO2006/029697

PCT Pub. Date: Mar. 23, 2006

(65) Prior Publication Data

US 2007/0282113 A1    Dec. 6, 2007

(30) Foreign Application Priority Data

Sep. 17, 2004    (IT)    .......................... MI2004A1769

(51) Int. Cl.
*A61K 31/404*    (2006.01)

(52) U.S. Cl. ..................................... 514/416

(58) Field of Classification Search ................. 514/416
See application file for complete search history.

(56) References Cited

U.S. PATENT DOCUMENTS

2007/0015922 A1    1/2007    Caldararo et al.

FOREIGN PATENT DOCUMENTS

WO    2004 078720    9/2004

OTHER PUBLICATIONS

Firouzabadi, et al. J. Chem. Soc., Perkin Trans I, (2002) pp. 2601-2604.*
Griffiths, P. G. et al., "Synthesis of the Radical Scavenger 1, 1, 3, 3-Tetramethylisoindolin-2-yloxyl", Aust. J. Chem., vol. 36, No. 2, pp. 397-401, 1983.
U.S. Appl. No. 12/161,283, filed Jul. 17, 2008, Caldararo, et al.

* cited by examiner

*Primary Examiner*—Rebecca L Anderson
*Assistant Examiner*—Shawquia Young
(74) *Attorney, Agent, or Firm*—Oblon, Spivak, McClelland, Maier & Neustadt, L.L.P.

(57) ABSTRACT

Process for the preparation of stable nitroxide radicals (I) starting from N-benzylphthalimide in three steps. In the first step, the N-benzylphthalimide is transformed into N-benzyl-1,1,3,3-tetralkylisoindoline by treatment with a Grignard reagent prepared in methyl-tert-butyl ether. In the second step, the N-benzyl-1,1,3,3-tetraalkylisoindoline is transformed into 1,1,3,3-tetra-alkylisoindoline by hydrogenolysis. In the third step, the 1,1,3,3-tetra-alkyl-isoindoline is transformed into the nitroxide radical by oxidation with hydrogen peroxide in the presence of a catalyst selected from acids and salts of polymolybdic or polytungstic acids.

28 Claims, No Drawings

PERFECTED PROCESS FOR THE PREPARATION OF STABLE NITROXIDE RADICALS

The present invention relates to a perfected process for the preparation of stable nitroxide radicals having general formula (I):

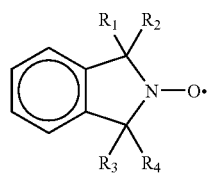
(I)

wherein $R_1$, $R_2$, $R_3$ and $R_4$, the same or different, represent alkyl or isoalkyl groups containing from 1 to 8 carbon atoms.

These stable nitroxide radicals are used as intermediates in the synthesis of more complex molecules or as initiators of radicalic reactions and, in particular, polymerization reactions. For this purpose, they are prepared by the oxidation with hydrogen peroxide of the corresponding secondary amines, 1,1,3,3-tetra-alkylisoindolines having formula (II):

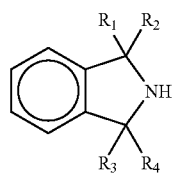
(II)

in the presence of catalysts based on tungstates, as described, for example, by P. G. Griffiths, G. Moad, E. Rizzardo, D. H. Solomon, in "Australian Journal of Chemistry", 1983, 36, 397.

The 1,1,3,3-tetra-alkylisoindolines having formula (II) can, in turn, be prepared by the cyclodimerization of dipropargyl amines and acetylenes in the presence of catalysts based on nickel (G. P. Chiusoli, L. Pallini, G. Terenghi, "Transition Metal Chemistry", 1983, 8, 189) or cobalt (G. P. Chiusoli, L. Pallini, G. Terenghi, "Transition Metal Chemistry", 1984, 9, 360) or the by carbonylation, in the presence of catalysts based on palladium, of dipropargyl amines (G. P. Chiusoli, M. Costa, S. Reverberi, G. Salerno, M. G. Terenghi, "Gazzetta Chimica Italiana" 1987, 117, 695). These synthesis methods, however, are jeopardized by the necessity of preparing the 1,6-diacetylenes (dipropargyl amines) used as raw materials.

The synthesis developed by Rizzardo and coworkers is of greatest practical interest. This envisages, as first step, the reaction of N-benzylphthalimide with a Grignard reagent. In the synthesis of 1,1,3,3-tetramethylisoindoline, for example, the Grignard reagent was prepared starting from methyl iodide and magnesium using, as solvents, ethyl ether and toluene (in succession): after 4 hours at reflux temperature, N-benzyl-1,1,3,3-tetramethylisoindoline was obtained (37% yield), which was then treated with hydrogen (4 atmospheres; room temperature) in glacial acetic acid and in the presence of catalysts based on palladium at 5% on coal. After 3 hours of reaction, 1,1,3,3-tetramethylisoindoline was obtained (II, $R=CH_3$) with a yield of 96% (P. G. Griffiths, G. Moad, E. Rizzardo, D. H. Solomon, "Australian Journal of Chemistry" 1983, 36, 397).

More recently, international patent application PCT/EP2004/002071 describes a synthesis method which allows tetra-alkylisoindolines to be prepared:
avoiding the use, in the Grignard reaction, of ethyl ether (a highly flammable solvent which easily gives rise to the formation of peroxides which, in turn, carry the risk of explosion) or its mixtures; and
carrying out the subsequent hydrogenolysis at atmospheric pressure thus eliminating the necessity of adopting equipment suitable for operating under pressure and simplifying the processes.

Also in this case, however, there are various problems mainly linked to the necessity of purifying the N-benzyl-1,1,3,3-tetra-alkylisoindolines, after the Grignard reaction, by chromatography on a basic alumina column, a procedure which is long and costly (particularly on an industrial scale).

The Applicant has now found that it is possible to prepare stable nitrosilic radicals according to a substantially simpler process than those described so far and which solves the relative problems. In particular, this perfected process allows:
N-benzyl-1,1,3,3-tetra-alkylisoindolines to be obtained, with a sufficient degree of purity to be used in subsequent steps without any purification (thus avoiding column chromatography); and
polymeric acids of molybdenum (or tungsten) which, as will appear more evident hereunder, are more advantageous than tungstates, to be used as catalysts in oxidation with hydrogen peroxide.

According to this improved process, described in the enclosed claims, stable nitrosilic radicals having formula (I) are prepared in three successive steps starting from N-benzylphthalimide which, although not a commercial product, can be easily and rapidly prepared by treating an alkaline salt of phthalimide with benzyl bromide or chloride or (and preferably) by the reaction of phthalic anhydride with benzyl amine.

In the first passage of the process, the N-benzyl phthalimide is transformed into an N-benzyl-1,1,3,3-tetra-alkylisoindoline by treatment with a Grignard reagent prepared in methyl-tert-butyl ether, a less volatile solvent than ethyl ether (and therefore less subject to catching fire) and which does not form peroxides, starting from magnesium and a $C_1$-$C_4$ alkyl halide.

Iodides, bromides or chlorides can be used as alkyl halides. They are normally used in an equimolecular amount with magnesium or in the presence of an excess (generally up to 10%, but also from 3 to 9%) of one or the other reagent.

The alkyl halide/N-benzylphthalimide molar ratio can, in turn, range from 4 to 10 and can be optimized each time, according to the higher or lower reactivity of the halide selected and/or of the Grignard reagent produced from the halide. The best results are normally obtained with ratios ranging from 5 to 9.

The selection of the solvent is particularly important. It is well known, in fact, that Grignard reagents must be prepared in ethers. If the reaction with N-benzylphthalimide, however, is carried out in the presence of an ether, it stops at intermediate products, mostly containing hydroxyl groups. It is therefore necessary to prepare the Grignard reagent in ether and then use it in another solvent having a higher boiling point (generally an aromatic solvent such as toluene). The ether can then be removed by distillation during the course of the reaction which, in this way, is completed and gives the desired products. This necessity makes many of the ethers normally used for preparing Grignard reagents, unusable, for example butyl ether ([n-C$_4$H$_9$]$_2$O having a boiling point of 142-143° C.) or butyl diglima ([n-C$_4$H$_9$OCH$_2$CH$_2$]$_2$O having a boiling point of 256° C.). Tetrahydrofuran, even if widely used for preparing Grignard reagents, surprisingly gives poor yields in the tetra-alkylation of N-benzylphthalimide. Methyl-tert-butyl ether, on the other hand, is an optimal solvent as, even if considerably less volatile than ethyl ether, has an acceptable boiling point (55-56° C.) and does not give rise to the formation of peroxides.

A partial oxidation with air of the reaction mixture is carried out at the end of the reaction. N-hexane is added at the end of the Grignard reaction, in order to obtain this partial oxidation, and the whole mixture is stirred in air for 3 to 5 hours. During this time, most of the impurities are oxidized producing insoluble materials. At the same time, the colour of the suspended solid products becomes deep violet, whereas the organic phase remains straw yellow. At the end, the reaction raw product is filtered on a celite panel, the filtrate is recovered and the solvents are removed under reduced pressure, obtaining N-benzyl-1,1,3,3-tetra-alkylisoindoline having such a purity as to allow it to be used in the subsequent passages without further purification.

In the second passage of the improved process, the N-benzyl-1,1,3,3-tetra-alkylisoindolines are transformed into 1,1,3,3-tetra-alkylisoindolines by treatment with hydrogen in glacial acetic acid and in the presence of catalysts based on palladium at 5% on coal. The reaction is preferably carried out at atmospheric pressure.

In the third and last passage of the improved process, object of the present invention, the 1,1,3,3-tetra-alkylisoindolines are transformed into nitroxide radicals by oxidation with hydrogen peroxide in the presence of suitable catalysts. As already specified, the prior art recommends the use of catalysts based on tungstates, but the Applicant has now found that the use of polymeric acids (or their salts) of molybdenum or tungsten has various advantages. The characteristic of molybdenum and tungsten of giving rise to a whole series of polymeric acids (polymolybdic and polytungstic) which, sometimes, can also incorporate different elements such as phosphorous, silicon, etc. (heteropolyacids), is well known. These acids and their ammonium salts or salts of alkaline metals are also capable of catalyzing the oxidation of 1,1,3,3-tetra-alkylisoindolines with hydrogen peroxide: it is in fact possible to use, for example, ammonium heptamolybdate [(NH$_4$)$_6$Mo$_7$O$_{24}$.4 H$_2$O], ammonium paratungstate [(NH$_4$)$_{10}$W$_{12}$O$_{41}$], ammonium metatungstate [(NH$_4$)$_6$W$_{12}$O$_{39}$.x H$_2$O] or peroxidic phosphotungstates of tetra-alkylammonium such as [(n-C$_8$H$_{17}$)$_3$NCH$_3$]$_3$PW$_4$O$_{24}$ (C. Venturello, R. D'Aloisio, "Journal of Organic Chemistry" 1988, 53, 1553). The use of polymolybdate salts is particularly convenient: these are just as efficient as tungstates but are less costly and, in addition, their solutions in the presence of hydrogen peroxide are of a dark orange colour which turns to yellow when the concentration of hydrogen peroxide becomes negligible. This colour variation allows an easy and effective monitoring of the reaction trend.

According to the process improved by the Applicant, the oxidation of 1,1,3,3-tetra-alkylisoindolines with hydrogen peroxide is preferably carried out in polar solvents (for example water, methanol, acetonitrile or their mixtures), with temperatures which can generally vary from 0 to 60° C. and at atmospheric pressure. The duration of the reaction depends on the conditions adopted and, in particular, on the temperature, nature and concentration of the substrate, on the concentration of hydrogen peroxide and on the nature and quantity of the catalyst.

If catalysts based on tungstates are used, the prior art suggests carrying out the reaction at room temperature for very long times, even 32 hours (P. G. Griffiths, G. Moad. E. Rizzardo, D. H. Solomon, "Australian Journal of Chemistry" 1983, 36, 397) or, with particular substrates, even 10 days (E. G. Rozantsev, V. D. Sholle, "Synthesis" 1971, 190). The Applicant, conversely, has found that it is more convenient to operate at moderate temperatures but higher than room temperature, preferably ranging from 40 to 50° C. Under these conditions, the reaction is complete in much shorter times, normally ranging from 2 to 5 hours.

The concentration of hydrogen peroxide used as oxidant is not critical: solutions of hydrogen peroxide (aqueous or in an organic solvent) can be used, with concentrations ranging from 1 to 90%. It turns out particularly safe and effective to use commercial 30% aqueous solutions in such quantities that the hydrogen peroxide/substrate ratio in moles ranges from 1.5 to 20.

As mentioned above, the duration of the reaction also depends on the substrate/catalyst ratio. Expressing this ratio as:

(moles of substrate)/(gram-atoms of metal)

convenient durations are obtained with ratios ranging from 10 to 50.

The improved process for the preparation of stable nitroxide radicals, object of the present invention, is now described by means of the following example, provided for purely illustrative and non-limiting purposes.

EXAMPLE

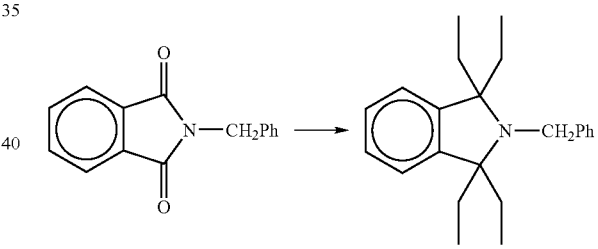

a) Synthesis of
N-benzyl-1,1,3,3-tetra-ethylisoindoline 8.75 g (360 mmoles) of magnesium turnings, 20 ml of anhydrous methyl-tert-butyl ether and 2 drops of dibromoethane, are charged under inert atmosphere. 26.5 ml (38.7 g; 355 mmoles) of ethyl bromide diluted in 100 ml of methyl-tert-butyl ether are added dropwise at such a rate as to maintain the solvent at reflux temperature. At the end of the addition, most of the methyl-tert-butyl ether is evaporated and a solution of 10 g of N-benzylphthalimide (42 mmoles) in 250 ml of anhydrous toluene are then added at such a rate as to allow a temperature of 80° C. to be reached and maintained. The residual methyl-tert-butyl ether is contemporaneously removed, by distillation. At the end of the addition, the removal of methyl-tert-butyl ether is completed, the mixture is brought to reflux temperature (about 110° C.), and is subsequently stirred at this temperature for a further 4 hours. After possibly verifying (by means of GC) the complete conversion of the substrate, the reaction mixture is cooled to room temperature, n-hexane is added and the mixture is stirred in air for 4 hours. At the end, the mixture is filtered on celite and the filtrate obtained (of a straw yellow colour) is dried. 6.0 g of N-benzyl-1,1,3,3-tetra-ethylisoindoline are obtained with a gas-chromatographic purity of 89% (17 mmoles; yield 40%).

b) Synthesis of 1,1,3,3-tetra-ethylisoindoline

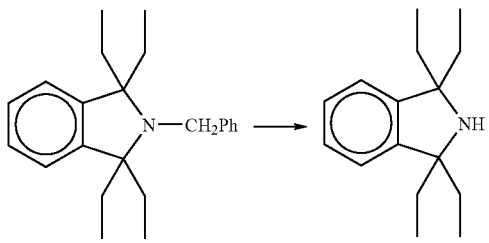

100 ml of glacial acetic acid, 6.0 g of 89% N-benzyl-1,1,3,3-tetra-ethylisoindoline (17 mmoles) and 1 g of 5% palladium on carbon are charged, under inert atmosphere, into a glass reactor.

The reactor is placed in a hydrogen atmosphere and the mixture is stirred at atmospheric pressure and room temperature for 3 hours, after which the complete conversion of the substrate is verified by means of GC and TLC. The reaction mixture is filtered on celite and the panel is washed with acetic acid. The acetic acid is removed by distilling it at reduced pressure, obtaining an oily residue to which water is added. This is then basified to pH 9 with 10% aqueous sodium hydroxide. The product is extracted with ethyl ether. The extracts are collected, dried on anhydrous sodium sulfate, filtered, and the solvent is removed at reduced pressure thus obtaining 4.25 g of 1,1,3,3-tetra-ethylisoindoline with a gas-chromatographic purity of 88% (16.2 mmoles; 95% yield).

c) Synthesis of 1,1,3,3-tetra-ethylisoindolin-2-yloxyl

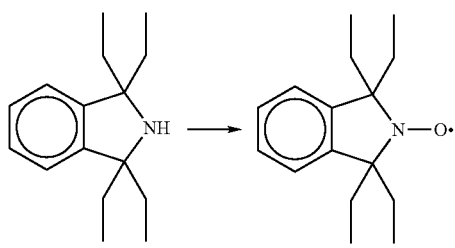

The following products are charged, in this order, into a 100 ml flask, equipped with magnetic stirring, thermometer, reflux cooler and drip funnel: 4.25 g of 88% 1,1,3,3-tetra-ethylisoindoline (16.2 mmoles), 35 ml of methanol, 3 ml of acetonitrile, 1.36 g of sodium bicarbonate (16.2 mmoles) and 180 mg of ammonium heptamolybdate [$(NH_4)_6Mo_7O_{24} \cdot 4 H_2O$]; 0.146 mmoles, corresponding to 1 mmole of molybdenum]. Once the reaction mixture has been heated to 45° C., 30 ml of 30% aqueous hydrogen peroxide are added dropwise, regulating the addition rate on the basis of the consumption of hydrogen peroxide which is indicated, each time, by the colour change of the reaction mass from dark orange to bright yellow. The whole addition of hydrogen peroxide and the subsequent completion of the reaction require 2 hours. At the end, brine is added and the reaction mixture is subsequently extracted with ethyl ether. The ether extracts are collected, washed with 1 N sulfuric acid and then with water (until neutrality), dried on sodium sulfate and filtered. The ether is removed by evaporation and the residue is purified by chromatography on a silica gel column using, as eluant, a 95:5 mixture of n-hexane and ethyl acetate. 3.50 g of 1,1,3,3-tetra-ethylisoindolin-2-yloxyl (14.2 mmoles; 88% yield) are obtained.

The invention claimed is:

1. A process for preparing a stable nitroxide radical compound of formula (I):

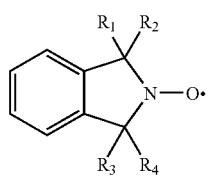

wherein $R_1$, $R_2$, $R_3$ and $R_4$, which may be the same or different, represent alkyl or isoalkyl groups having from 1 to 8 carbon atoms, wherein said process comprises:

a) preparing an N-benzyl-1,1,3,3-tetra-alkylisoindoline intermediate in a reaction mixture by reacting in the presence of an aromatic solvent an N-benzylphthalimide with a Grignard reagent formed by reacting in the presence of a methyl tertiary butyl ether solvent an alkyl halide with magnesium;

(b) removing said methyl tertiary butyl ether solvent by continuously distilling during said preparing;

(c) purifying said reaction mixture by oxidizing impurities present within said reaction mixture with air while stirring for a period of 3 to 5 hours to produce insolubilized oxidized impurities;

(d) removing said insolubilized oxidized impurities from said reaction mixture by filtering said reaction mixture on a celite panel to obtain a purified filtrate;

(e) isolating said N-benzyl-1,1,3,3-tetra-alkylisoindoline intermediate by removing said aromatic solvent from said purified filtrate;

(f) forming a 1,1,3,3-tetra-alkylisoindoline by subjecting said isolated N-benzyl-1,1,3,3-tetra-alkylisoindoline intermediate to hydrogenolysis in the presence of hydrogen and a supported palladium catalyst, at room temperature and at atmospheric pressure; and (g) yielding a stable nitroxide radical of formula (I) by oxidizing said 1,1,3,3-tetra-alkylisoindoline with hydrogen peroxide in the presence of a catalyst selected from polymolybdic acids, polytungstic acids, and salts thereof, optionally incorporating an element selected from phosphorus and silicon.

2. The process according to claim 1, wherein said aromatic solvent is toluene.

3. The process according to claim 1, wherein said N-benzylphthalimide is prepared by treating a phthalimide alkaline salt with a benzyl halide.

4. The process according to claim 1, wherein said N-benzylphthalimide is prepared by reacting phthalic anhydride with benzylamine.

5. The process according to claim 1, wherein said alkyl halide is present in an excess amount of up to 10 wt. % with respect to said magnesium.

6. The process according to claim 1, wherein said magnesium is present in an excess amount of up to 10 wt. % with respect to said alkyl halide.

7. The process according to claim 1, wherein the molar ratio of said alkyl halide to said N-benzylphthalimide ranges from 4 to 10.

8. The process according to claim 1, wherein said oxidizing of said impurities present within said reaction mixture is carried out in the presence of n-hexane.

9. The process according to claim 1, wherein said isolating of said N-benzyl-1,1,3,3-tetra-alkylisoindoline intermediate by removing said aromatic solvent from said purified filtrate is carried out by drying under reduced pressure.

10. The process according to claim 1, wherein said hydrogen is provided by glacial acetic acid.

11. The process according to claim 1, wherein said supported palladium catalyst consists of a palladium catalyst on carbon.

12. The process according to claim 1, wherein the molar ratio of said isolated N-benzyl-1,1,3,3-tetra-alkylisoindoline intermediate to said supported palladium catalyst ranges from 10 to 50.

13. The process according to claim 1, wherein said oxidizing of said 1,1,3,3-tetra-alkylisoindoline with hydrogen peroxide is carried out at a temperature ranging from 0° C. to 60° C. and at atmospheric pressure.

14. The process according to claim 13, wherein said oxidizing of said 1,1,3,3-tetra-alkylisoindoline with hydrogen peroxide is carried out at a temperature ranging from 40° C. to 50° C.

15. The process according to claim 1, wherein said oxidizing of said 1,1,3,3-tetra-alkylisoindoline with hydrogen peroxide is carried out in the presence of a catalyst and a polar solvent.

16. The process according to claim 15, wherein said polar solvent is selected from water, methanol, acetonitrile, and mixtures thereof.

17. The process according to claim 1, wherein said hydrogen peroxide is a solution of hydrogen peroxide dissolved in a solvent selected from water and organic solvents.

18. The process according to claim 17, wherein said solution of hydrogen peroxide is a 30% aqueous hydrogen peroxide solution.

19. The process according to claim 1, wherein the molar ratio of said hydrogen peroxide to said 1,1,3,3-tetra-alkylisoindoline ranges from 1.5 to 20.

20. The process according to claim 1, wherein the molar ratio of said 1,1,3,3-tetra-alkylisoindoline to said catalyst ranges from 10 to 50.

21. The process according to claim 1, wherein said polymolybdic salt and said polytungstic salt are selected from ammonium salts and salts of alkali metals.

22. The process according to claim 1, wherein said catalyst is ammonium heptamolybdate.

23. The process according to claim 1, wherein said catalyst is selected from ammonium paratungstate and ammonium metatungstate.

24. The process according to claim 1, wherein said catalyst is selected from polymolybdic acids, polytungstic acids, and salts thereof, incorporating phosphorus.

25. The process according to claim 1, wherein said catalyst is selected from polymolybdic acids, polytungstic acids, and salts thereof, incorporating silicon.

26. The process according to claim 1, wherein said catalyst is selected from polymolybdic acids, polytungstic acids, and salts thereof, not incorporating an element selected from phosphorus and silicon.

27. The process according to claim 26, wherein said catalyst is selected from polymolybdic acids and salts thereof.

28. The process according to claim 26, wherein said catalyst is selected from polytungstic acids and salts thereof.

* * * * *